US010883081B2

(12) United States Patent
Adams et al.

(10) Patent No.: US 10,883,081 B2
(45) Date of Patent: Jan. 5, 2021

(54) SYSTEMS, METHODS AND APPARATUSES FOR PROCESSING PLANT EMBRYOS

(71) Applicant: J.D. IRVING, LIMITED, St. John (CA)

(72) Inventors: Gregory W. Adams, Sussex Corner (CA); Andrew W. McCartney, Plumweseep (CA); John F. Lawless, Quispamsis (CA); John Aikens, New Maryland (CA); Chris Davenport, Keswick Ridge (CA)

(73) Assignee: J. D. Irving, Limited, Saint John (CA)

( * ) Notice: Subject to any disclaimer, the term of this patent is extended or adjusted under 35 U.S.C. 154(b) by 276 days.

(21) Appl. No.: 15/847,397

(22) Filed: Dec. 19, 2017

(65) Prior Publication Data

US 2018/0171289 A1 Jun. 21, 2018

Related U.S. Application Data

(60) Provisional application No. 62/436,598, filed on Dec. 20, 2016.

(51) Int. Cl.
*A01G 2/00* (2018.01)
*A01G 7/00* (2006.01)
*A01H 4/00* (2006.01)
*C12N 5/04* (2006.01)
*C12M 1/36* (2006.01)
*C12M 1/06* (2006.01)
*C12M 1/26* (2006.01)
(Continued)

(52) U.S. Cl.
CPC .................. *C12N 5/04* (2013.01); *A01G 2/00* (2018.02); *A01G 7/00* (2013.01); *A01H 4/005* (2013.01); *A01H 4/006* (2013.01); *C12M 23/04* (2013.01); *C12M 27/02* (2013.01); *C12M 33/04* (2013.01); *C12M 41/48* (2013.01); *C12M 47/04* (2013.01)

(58) Field of Classification Search
CPC ... A01G 2/00; A01G 7/00; A01H 4/00; A01H 4/005; A01H 4/006
USPC ............ 47/1.01 R; 435/410, 420, 430, 430.1
See application file for complete search history.

(56) References Cited

U.S. PATENT DOCUMENTS 6,684,564 B1 * 2/2004 Hirahara .................. A01C 1/06
47/57.6
7,568,309 B2 * 8/2009 Hirahara ................ A01H 4/006
47/57.6
(Continued)

FOREIGN PATENT DOCUMENTS

EP          1535868 A1    6/2005
WO          0113702 A2    3/2001

*Primary Examiner* — David J Parsley
(74) *Attorney, Agent, or Firm* — Bereskin & Parr LLP; Carmela De Luca

(57) ABSTRACT

A pick-and-place system for plant embryos includes a tray for receiving a suspension of plant embryos. The tray is movable to repeatedly reposition the plant embryos. An identification system is proximate the tray for identifying a target plant embryo amongst the plant embryos in the suspension. The identification system is configured to identify the target plant embryo while the tray is moving. A robotic arm is proximate the tray and is in communication with the identification system. The robotic arm is actuatable to pick the target plant embryo out of the suspension while the tray is moving, and deposit the target plant embryo at a target location.

22 Claims, 15 Drawing Sheets

(51) Int. Cl.
    *C12M 1/12*           (2006.01)
    *C12M 1/00*           (2006.01)

(56) References Cited

U.S. PATENT DOCUMENTS

| | | | |
|---|---|---|---|
| 8,216,841 B2 * | 7/2012 | Nehra | A01H 4/001 |
| | | | 435/422 |
| 8,931,208 B2 | 1/2015 | Swanda et al. | |
| 9,113,592 B2 * | 8/2015 | Rubatino | A01H 4/006 |
| 9,320,209 B2 * | 4/2016 | Cootsona | A01H 4/00 |
| 9,335,319 B2 | 5/2016 | Swanda | |
| 9,631,174 B2 * | 4/2017 | Aidun | C12N 5/04 |
| 2006/0032121 A1 | 2/2006 | Hirahara | |
| 2015/0284672 A1 | 10/2015 | Swanda et al. | |

* cited by examiner

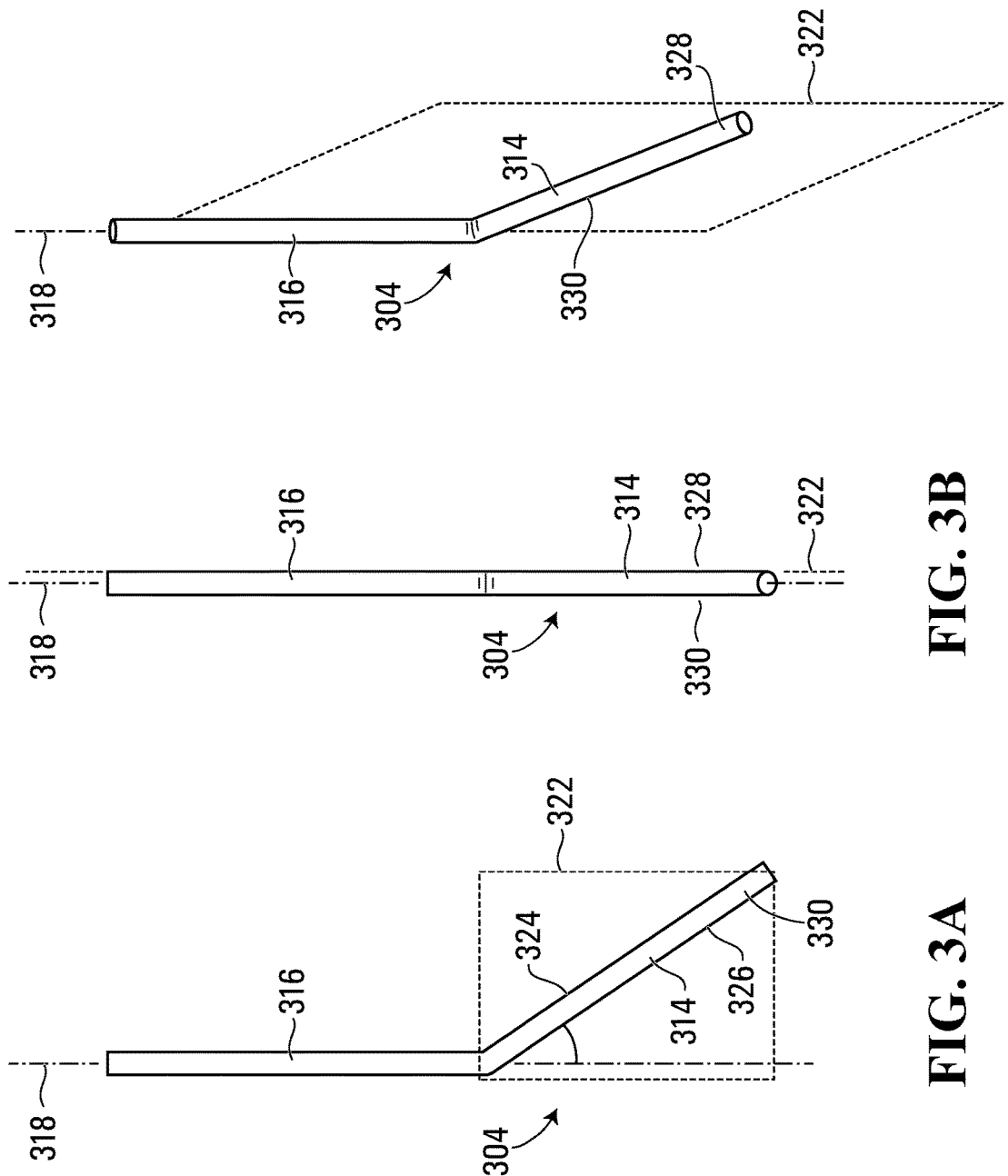

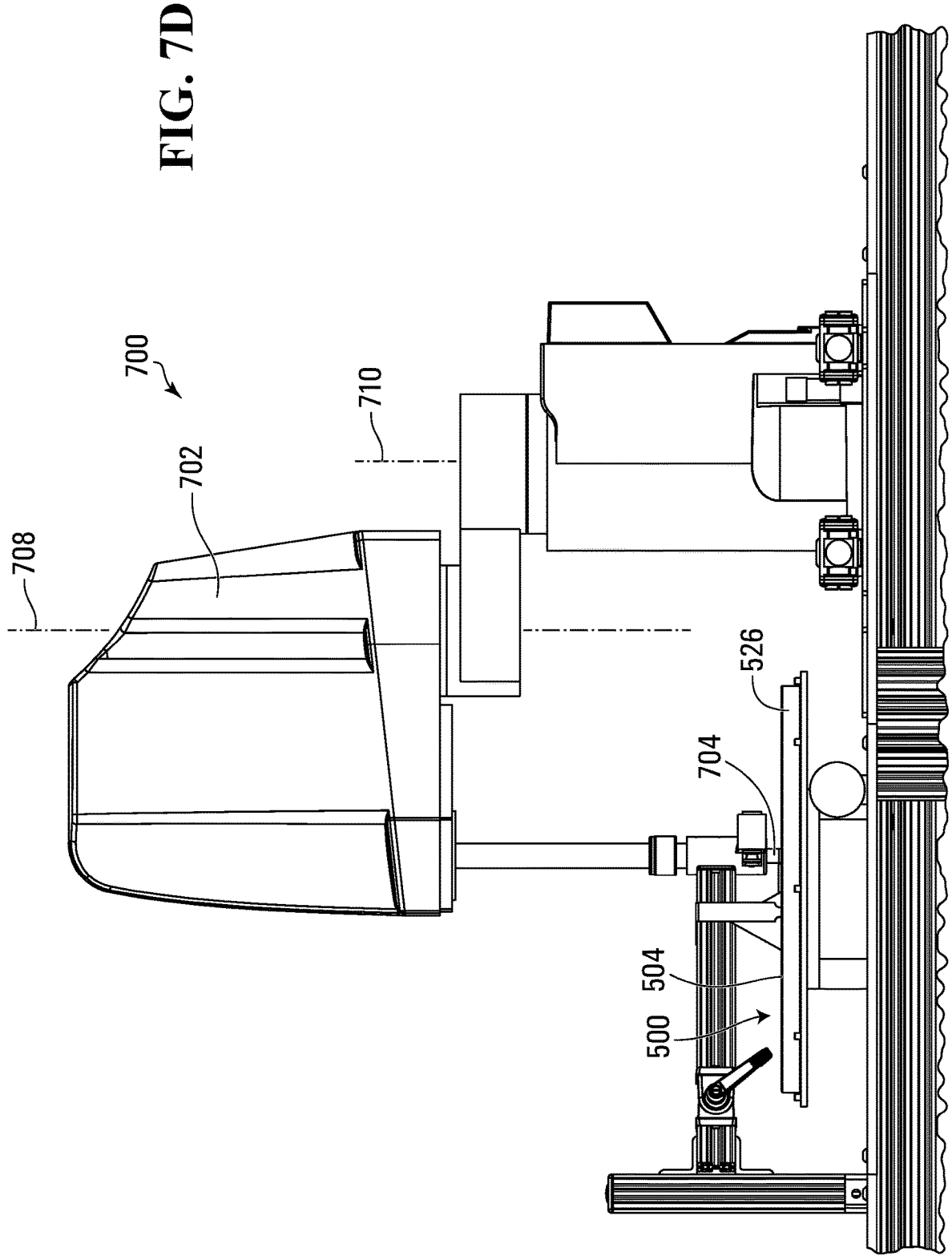

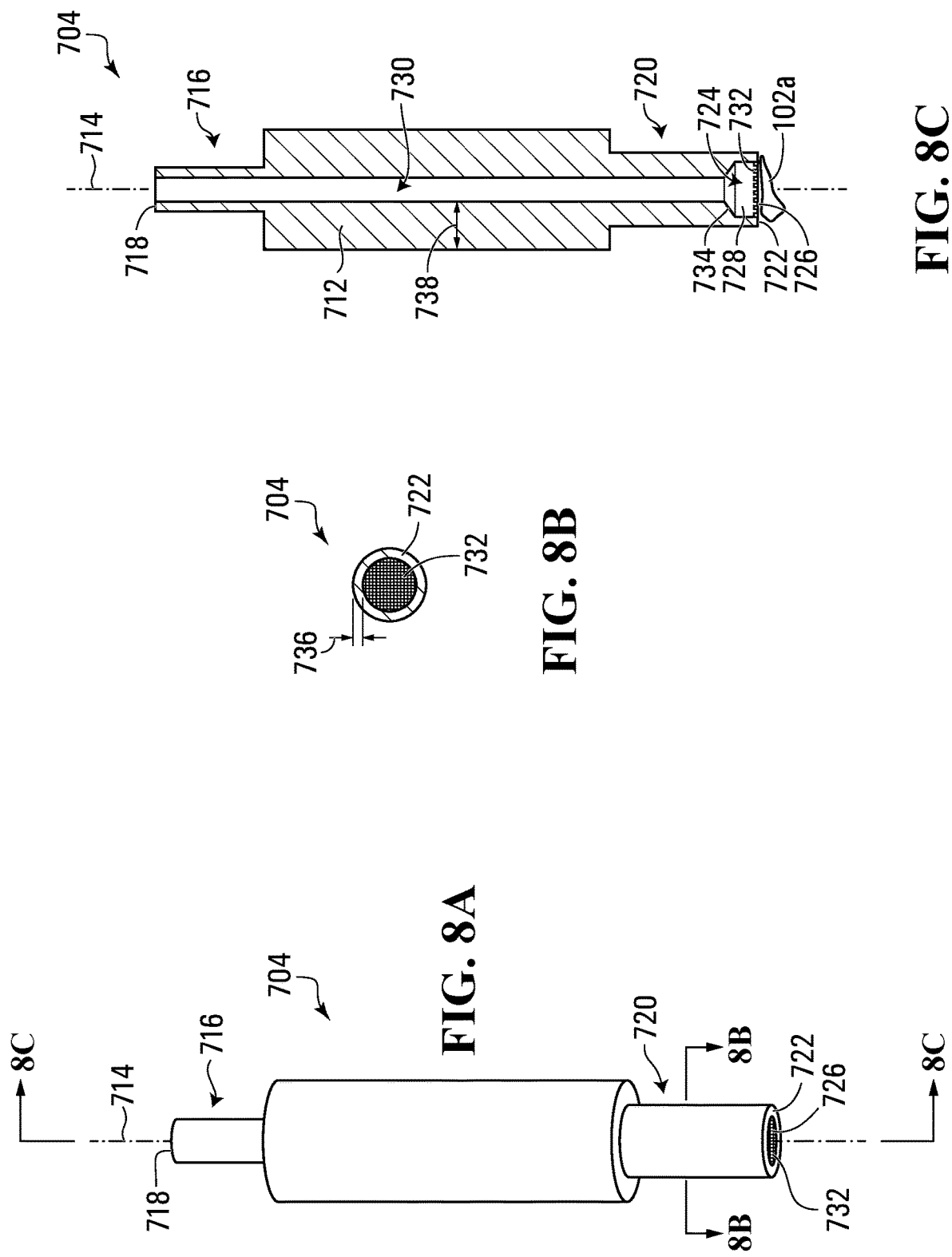

SYSTEMS, METHODS AND APPARATUSES FOR PROCESSING PLANT EMBRYOS

CROSS-REFERENCE TO RELATED APPLICATIONS

This application claims priority from U.S. Provisional patent application Ser. No. 62/436,598 filed Dec. 20, 2016; which is incorporated herein in its entirety by reference.

FIELD

The disclosure relates to the in vitro culture of plant embryos. More specifically, the disclosure relates to systems, methods, and apparatuses for processing plant embryos that have been developed in vitro.

BACKGROUND

U.S. Pat. No. 9,335,319 (Swanda) discloses a method of singulating embryos. The method includes providing a plurality of embryos within a system and sensing at least one of the plurality of embryos in a fluid. The method also includes dispensing at least one of the plurality of embryos on a surface.

U.S. Pat. No. 8,931,208 (Swanda) discloses an automated system and methods for separating and singulating plant embryos. The system includes: a separation module constructed and arranged to separate a plurality of plant embryos from attached embryogenic suspensor mass, and sort the plant embryos according to size; a singulation module constructed and arranged to singulate the separated and sorted plant embryos into individual, discrete embryos, and to deposit the singulated embryos onto a porous substrate; a drying module constructed and arranged to dry the porous substrate upon which the singulated plant embryos are disposed; and a robotic arm operable to transport the plant embryos from module to module in a predetermined sequence. The robotic arm is programmable such that the robotic arm is not limited to move from module to module in the predetermined sequence. The robotic arm may move among the modules in response to one or more signals, and perform functions associated with separating and singulating plant embryos in addition to transporting the plant embryos from module to module, thereby optimizing the transport of plant embryos through the system and maximizing the use of each module to separate and singulate plant embryos. The automated system for separating and singulating plant embryos may further include a storage module for storing the plant embryos before the plant embryos are transported to the separation module. The automated system for separating and singulating plant embryos may further include a docking module for receiving plant embryos from the drying module, and for storing the plant embryos in containers that provide an environment suitable for further maturation of the plant embryos.

U.S. Patent Application Publication No. 2015/0284672 (Swanda et al.) discloses separating and singulating embryos by employing a spray module configured to spray a plurality of embryos which are loaded on a porous substrate so as to separate and singulate the plurality of embryos, and a drying module configured to dry the plurality of separated and singulated embryos retained on the porous substrate while the porous substrate is moved across the drying module. A robotic arm operates to transfer the porous substrate from module to module, and a control device controls the operation of the system of separating and singulating embryos.

SUMMARY

The following summary is intended to introduce the reader to various aspects of the disclosure, but not to define or delimit any invention.

According to some aspects, a pick-and-place method for plant embryos comprises: a) depositing a suspension of singulated plant embryos into a tray; b) moving the tray; c) while moving the tray, identifying a target plant embryo amongst the plant embryos in the suspension in the tray; d) after step c) and while moving the tray, picking the target plant embryo out of the suspension in the tray; and e) after step d), depositing the target plant embryo at a target location.

Step a) may be carried out while moving the tray.

Moving the tray may comprise rotating the tray. The tray may have a base surface, and a central axis extending perpendicular to the base surface. Rotating the tray may comprise rotating the tray about the central axis.

Step a) may comprise flowing the suspension of plant embryos from a holding vessel into the tray. The method may further comprise flowing the suspension along a dispersion element into the tray. The dispersion element may comprise an upstream end spaced from the tray, a downstream end adjacent the tray, and a sidewall extending between the upstream end and downstream end. A cross-sectional area of the sidewall may increase from the upstream end to the downstream end. Step a) may comprise flowing the suspension of plant embryos along the sidewall. The sidewall may be conical. Step a) may comprise flowing the suspension along the sidewall in a dropwise fashion.

The tray may further comprise an outer rim extending upwardly from the base surface around a periphery of the base surface. The tray may further comprise an inner rim extending upwardly from the base surface. The outer rim may be taller than the inner rim. The method may further comprise draining the suspension of plant embryos via the inner rim during steps a) to e).

Step c) may comprise identifying the target plant embryo based on size. For example, step c) may comprise capturing images of the plant embryos in the suspension in the tray, analyzing the images, and identifying the target plant embryo based on the images. Step c) may further comprise illuminating the suspension in the tray with a colored light. The colored light may be a green light. In embodiments comprising illuminating the suspension.

Step d) may comprise actuating a robotic arm to pick the target plant embryo out of the suspension. The robotic arm may have a tip for handing the target plant embryo. Step d) may comprise rotating the tip about at least a first generally vertical robot axis. Step d) may further comprise moving the tip downwardly towards the tray to pick the target plant embryo out of the suspension. Step d) may further comprise applying a suction force to the tip to draw the target plant embryo towards the tip.

Step e) may comprise actuating the robotic arm to move the target plant embryo to the target location. Step e) may further comprise actuating the robotic arm to move the tip upwardly to clear an outer rim of the tray. Step e) may further comprise actuating the robotic arm to rotate the tip about at least the first generally vertical robot axis to move the tip away from the tray and towards the target location. Step e) may further comprise actuating the robotic arm to move the tip downwardly towards the target location. Step e) may further comprise applying a blowing force to release the target plant embryo from the tip.

The tip may comprise a conduit in fluid communication with a source of suction, and a screen upstream of the conduit and in fluid communication with the conduit. Step d) may comprise suctioning the first target plant embryo onto the screen. Step e) may comprise blowing the first target plant embryo off of the screen.

According to another aspect, a pick-and-place system for plant embryos comprises a tray for receiving a suspension of plant embryos. The tray is movable, optionally rotatable, to repeatedly reposition the plant embryos. An identification system is proximate the tray for identifying a target plant embryo amongst the plant embryos in the suspension in the tray. The identification system can be configured to identify the target plant embryo while the tray is moving, or while the tray is stationary, or both. A robotic arm is proximate the tray and in communication with the identification system. The robotic arm is actuatable to pick the target plant embryo out of the suspension in the tray while the tray is moving, and deposit the target plant embryo at a target location.

The tray may comprise a base surface and central axis that is perpendicular to the base surface. The tray may be movable by rotation about the central axis.

The tray may further comprise an outer rim extending upwardly from the base surface and around a periphery of the base surface. The tray may further comprise an inner rim extending upwardly from the base surface. The base surface may be annular and extend between the inner rim and the outer rim. The inner rim may define a drain of the tray.

The identification system may comprise a camera and an image processing system connected to the camera. The camera may be positioned to capture images of the plant embryos in the suspension as the tray is moved. The image processing system may be configured to analyze the images and identify the target plant embryo amongst the plant embryos in the suspension.

The image processing system may be configured to determine at least one parameter of the plant embryos based on the images. The at least one parameter may be size, which may be based on image intensity.

The identification system may further comprise a light positioned to illuminate the plant embryos in the suspension in the tray. The light may be a green light, which may accentuate image intensity and/or contrast.

The robotic arm may comprise a tip for handling the target plant embryo. The robotic arm may be actuatable to move the tip horizontally between the tray and the target location. The robotic arm may further be actuatable to move the tip downwardly towards the tray to pick the target plant embryo out of the suspension. The tip may be configured to apply suction to draw the target plant embryo towards the tip. The robotic arm may further be actuatable to move the tip upwardly to clear an outer rim of the tray. The robotic arm may further be actuatable to rotate the tip about at least a first generally vertical robot axis to move the tip horizontally away from the tray and towards the target location. The robotic arm may further be actuatable to move the tip downwardly towards the target location. The tip may be configured to apply a blowing force to release the target plant embryo from the tip.

The tip may comprise a screen for holding the first target plant embryo. The tip may further comprise a conduit between the screen and a source of suction for suctioning the target plant embryo onto the screen.

The system may further comprise a conduit for depositing the suspension of plant embryos into the tray. The conduit may have an inlet end portion for receiving the suspension of plant embryos and an outlet end portion for dispensing the suspension of plant embryos into the tray. The tray may be movable with respect to the outlet end portion to spread the suspension as the suspension is deposited into the tray.

The outlet end portion of the conduit may comprise a dispersion element for further spreading the suspension as the suspension is deposited into the tray. The dispersion element may be conical. The dispersion element may comprise an upstream end spaced from the tray, a downstream end adjacent the tray, and a sidewall extending therebetween. A cross-sectional area of the sidewall may increase from the upstream end to the downstream end. The sidewall may be in fluid communication with the inlet end portion and the tray.

According to another aspect, a tip for picking up plant embryos comprises a body. The body has a body proximal portion mountable to a robotic arm and an opposed body distal portion defining a body distal end. A bore extends into the body from the body distal end. The bore has a bore cross-sectional area. A conduit is in fluid communication with the bore. The conduit has a conduit cross-sectional area less than the bore cross-sectional area. The conduit extends from the bore and through the body and is connectable to a source of suction. A screen extends across the bore for holding the plant embryos.

The bore may have a bore distal end at the body distal end, and an opposed bore proximal end. The screen may be positioned at the bore distal end.

The body may comprise a shoulder at a junction of the bore and the conduit, and the shoulder may taper in cross-sectional area going from the bore to the conduit.

The body may have a wall thickness around the bore, and the wall thickness may be between about 0.25 mm and about 1.25 mm. In some examples, the wall thickness is between about 0.5 mm and about 1.0 mm.

The bore diameter may be between 1.5 and 4 times the conduit diameter. In some examples, the bore diameter area is between 2.0 and 2.5 times the conduit diameter.

According to another aspect, a method for maintaining singulated plant embryos in suspension comprises: a) supplying a suspension of the plant embryos in a liquid to a holding vessel; and b) immersing a rotational flow impeller in the suspension. The rotational flow impeller has at least a first blade. The first blade defines a plane of rotation. The method further comprises: c) stirring the suspension by rotating the rotational flow impeller about a generally vertical axis of rotation.

The first blade may be generally perpendicular to the plane of rotation.

Step c) may comprise inducing rotational flow in the holding vessel. Step c) may further comprise inhibiting radial flow. Step c) may further comprise inhibiting axial flow.

The method may further comprise rotating the rotational flow impeller at a speed selected to avoid the formation of a vortex in the holding vessel.

The first blade may be non-parallel to the axis of rotation. The first blade may be non-perpendicular to the axis of rotation.

The rotational flow impeller may be connected to a shaft, and the shaft may extend along the axis of rotation. The rotational flow impeller and the shaft may be integral.

In some examples, the holding vessel does not include any baffles.

In some examples, the first blade is exactly perpendicular to the plane of rotation.

According to some aspects, a system for maintaining singulated plant embryos in suspension comprises a holding vessel, and a suspension of separated plant embryos in a liquid within the holding vessel. A rotational flow impeller is immersed in the suspension. The rotational flow impeller is rotatable about a generally vertical axis of rotation. The rotation flow impeller has at least a first blade. The first blade defines a plane of rotation.

The first blade may be generally perpendicular to the plane of rotation.

The first blade may be generally non-parallel to the axis of rotation. The first blade may be generally non-perpendicular to the axis of rotation.

The rotational flow impeller may be connected to a shaft, and the shaft may extend along the axis of rotation. The rotational flow impeller and the shaft may be integral.

In some examples, the holding vessel does not include any baffles.

The method and/or system for maintaining singulated plant embryos in suspension is optionally used in pick and place methods and/or systems described herein.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art Preferred features of each aspect of the invention may be as described in connection with any of the other aspects. Other features of the invention will become apparent from the following examples. Generally speaking the invention extends to any novel one, or any novel combination, of the features disclosed in the this specification (including any accompanying claim and drawings). Thus features, characteristics or steps described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 3A is a side view of the rotational flow impeller of the holding module of FIG. 2;

FIG. 3B is a front view of the rotation flow impeller of FIG. 3A;

FIG. 3C is a perspective view of the rotational flow impeller of FIG. 3A;

FIG. 7D is a side view of the pick-and-place module of FIG. 1A, with the robotic arm in position to pick up a target plant embryo;

FIG. 8A is a perspective view of a tip of the robotic arm of FIGS. 6 to 7E;

FIG. 8B is a transverse section taken along line B-B in FIG. 8A; and

FIG. 8C is a longitudinal section taken along line C-C in FIG. 8A.

DETAILED DESCRIPTION

Figure 1A:
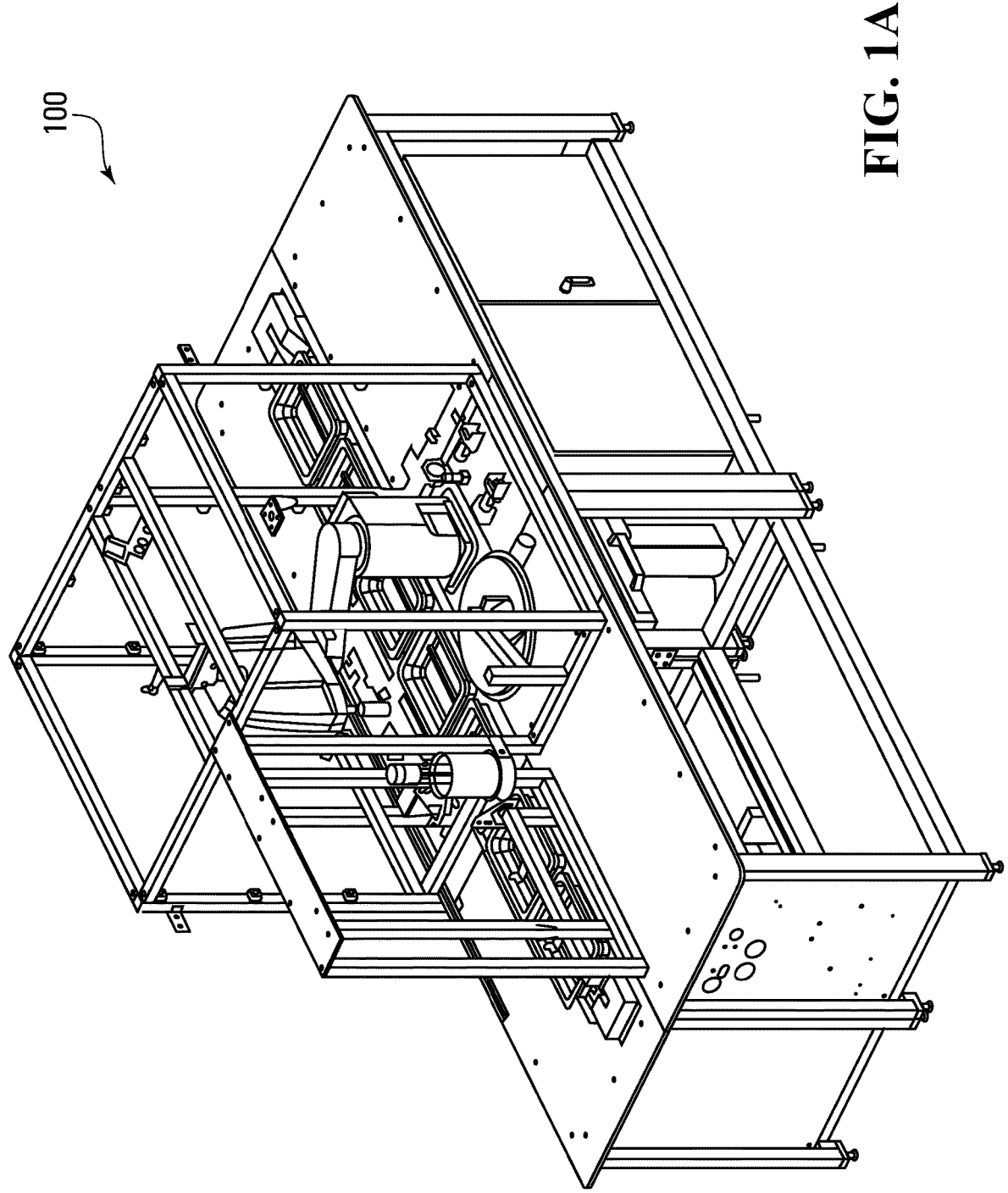
FIG. 1A is a perspective view of an example system for processing plant embryos.

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

The development of plant embryos in vitro may generally include four phases: (1) initiation or induction, to initiate formation of embryogenic tissue; (2) multiplication or maintenance, to multiply and mass produce embryogenic tissue; (3) development, to develop and form mature embryos; and (4) post development steps. Optionally, cryogenic storage may precede phase (1). Processes for carrying out phases (1) to (3) are known in the art, and will not be described in detail herein. The present disclosure relates to the fourth phase.

Upon completion of development of plant embryos in vitro (i.e. upon completion of phase (3)), the plant embryos may be attached to and/or embedded in residual tissues (e.g. embryogenic suspensor mass), and attached to other embryos (e.g. other healthy embryos, or other underdeveloped, incompletely developed, or abnormally developed embryos). Disclosed herein are systems, methods, and apparatuses for processing these plant embryos. More specifically, disclosed herein are systems, methods, and apparatuses for singulation of these plant embryos, as well as pick-and-place systems, methods, and apparatuses for the singulated plant embryos.

As used herein, the term "singulation" refers to a process whereby plant embryos that have been developed in vitro are separated from each other and/or cleaned of attached residual tissues. The term "singulation" includes processes in which all of the plant embryos in a given batch or group are fully separated from each other and fully cleaned of attached residual tissues, and processes in which only some of the plant embryos in a given batch or group are fully separated from each other and fully cleaned of attached residual tissues, and process in which some or all embryos in a given batch or group are partially separated from each other and/or partially cleaned of attached residual tissues.

The term "singulated plant embryos" (or simply "singulated embryos") refers to a batch or group of plant embryos that have undergone this singulation process, and as such includes batches or groups in which all of the plant embryos are fully separated from each other and fully cleaned of attached residual tissues, and in which only some of the plant embryos are fully separated from each other and fully cleaned of attached residual tissues, and in which some or all embryos are partially separated from each other and/or partially cleaned of attached residual tissues. Accordingly, the term "suspension of singulated plant embryos" can refer to a suspension in which some of the embryos are still attached to each other and to residual tissue, while some of the embryos are detached from any other embryos and any residual tissue.

The term "pick-and-place" refers to the processing of these singulated plant embryos as individual, discrete embryos. This processing of individual discrete embryos may include, for example, identifying embryos of a certain size amongst the singulated embryos, picking up the identified embryos, and placing the identified embryos into receiving plates.

Figure 1B:
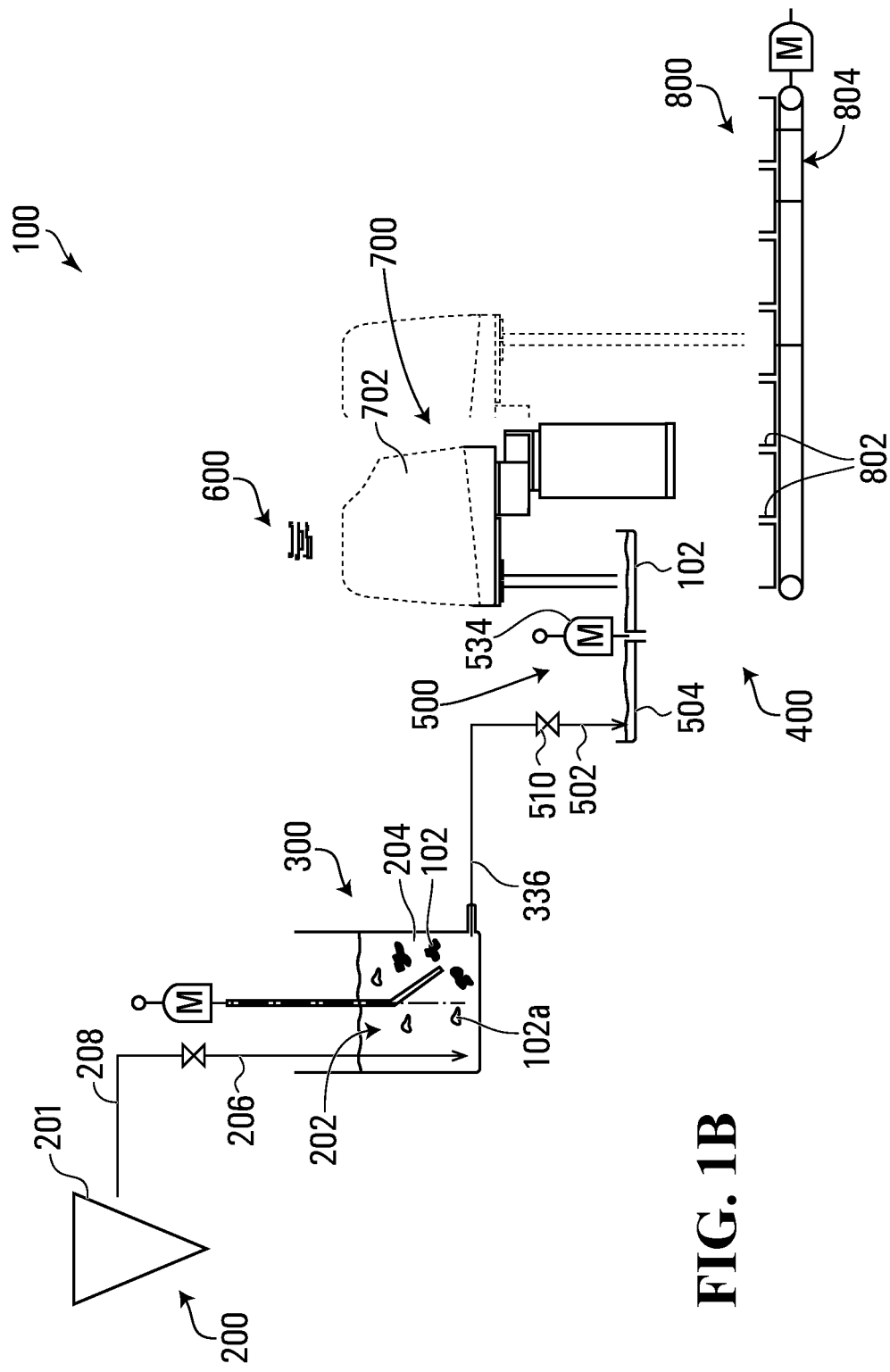
FIG. 1B is a schematic view of the system of FIG. 1A.

Referring now to FIGS. 1A and 1B, an example system 100 for processing plant embryos 102 (shown in FIG. 1B) is shown. The system 100 includes several modules (which may also be referred to herein as "systems", "sub-systems", or "assemblies"), including a singulation module 200 (shown in FIG. 1B), a holding module 300, and a pick-and-place module 400. The pick-and-place module 400 itself includes several modules, namely a preparation module 500, an identification module 600, and a handling module 700.

Referring to FIG. 1B, upon completion of the development phase, the plant embryos 102 are forwarded to the system 100, and particularly to the singulation module 200. For example, plant embryos 102 may be transferred from petri dishes (not shown) to the singulation module 200. In the singulation module, the plant embryos 102 undergo singulation as described above, to yield a suspension 202 of singulated plant embryos 102 in a liquid medium 204 (also referred to herein simply as a "suspension" or a "suspension of plant embryos").

Referring still to FIG. 1B, the singulation module 200 may be of any suitable configuration. In one particular example, the plant embryos 102 may be singulated by subjecting them to shear forces. For example, the plant embryos 102 may be added to a liquid medium in generally conical flask 201, where they are vortexed (e.g. using a vortex mixer). The shear forces experienced by the plant embryos 102 during vortexing can cause separation of the plant embryos 102 from each other and from attached residual tissue. After vortexing, the singulated plant embryos 102 may settle to the bottom of the flask 201, while the residual tissues and attached embryos may remain suspended in the liquid medium and/or may float to the surface of the liquid medium. The supernatant, containing the residual tissues and attached embryos, may be poured off, and fresh liquid medium may be added to the flask 201. Vortexing may then be repeated, optionally several times. The singulated embryos 102 in suspension may then be transferred to the holding module 300. The sediment in the flask 201 may optionally be re-suspended in addition liquid medium, and the vortexing may be repeated to singulate additional embryos.

In some examples, the subjecting to shear forces may be carried out in the absence of a stirring implement, such as an impeller. The high speed achieved during vortexing may be sufficient to cause singulation of the plant embryos 102, even in the absence of a stirring implement. Separating the plant embryos 102 without using a stirring implement may help to maintain the health of the plant embryos 102, as high speed collisions between the plant embryos 102 and a stirring implement, which can cause damage to the embryos, are avoided.

As noted above, from the singulation module 200, the suspension 202 is supplied to the holding module 300. For example, the suspension 202 may flow under the force of gravity from the singulation module 200, through a conduit 206 and a valve 208, and to the holding module 300. In the holding module 300, the plant embryos 102 are maintained in suspension, while awaiting processing in the pick-and-place module 400. The holding module 300 may also be referred to as a "system for maintaining separated plant embryos in suspension".

Figure 2:
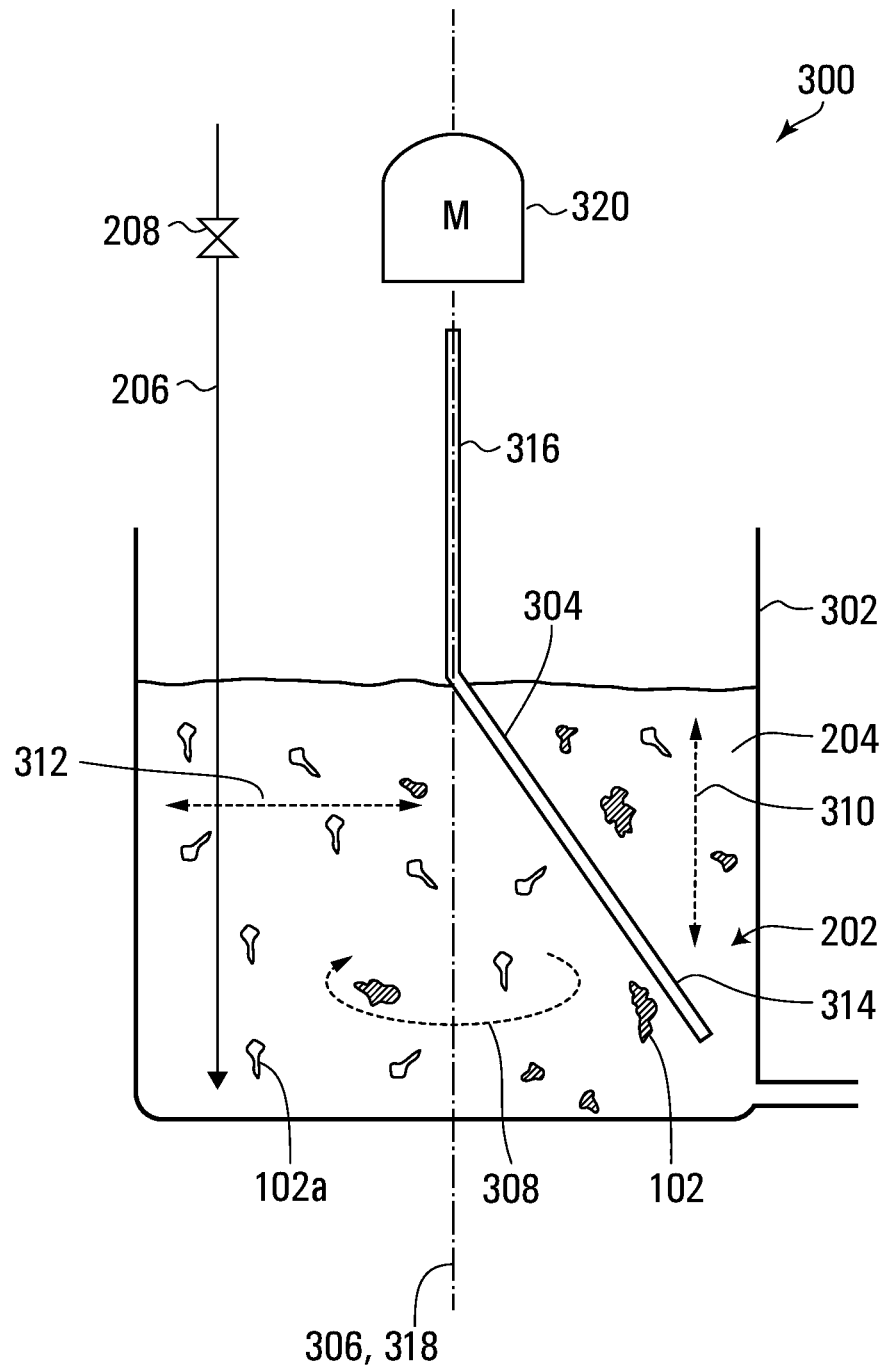
FIG. 2 is a schematic view of the holding module of the system of FIG. 1A.

Referring now to FIG. 2, in the example shown, the holding module 300 includes a holding vessel 302. The holding vessel 302 may be, for example, a beaker, a tank, or a vat. The suspension 202 is within the holding vessel 302.

The holding module 300 further includes an impeller 304, which is shown in further detail in FIGS. 3A to 3C, and which is immersed in the suspension 202 in the holding vessel 302. The impeller 304 facilitates rotational flow of the suspension 202 in the holding vessel 302, while limiting axial flow and radial flow, and may also be referred to as a "rotational flow impeller". More specifically, as shown in FIG. 2, the holding vessel 302 has a generally vertical longitudinal axis 306. The impeller 304 facilitates rotational flow around the longitudinal axis 306, as shown by arrow 308, while limiting flow parallel to the longitudinal axis 306 (i.e. axial flow), as shown by arrow 310, and limiting flow perpendicular to the longitudinal axis 306 (i.e. radial flow), as shown by arrow 312. This rotational flow pattern may prevent, inhibit, or minimize settling and clumping of the embryos 102 in the suspension 202, while being gentle enough to prevent, inhibit, or minimize damage to the embryos 102.

Referring still to FIGS. 3A to 3C, in the example shown, the impeller 304 is connected to a shaft 316, and includes a first blade 314 that extends from the shaft 316. In alternative examples, the impeller may include additional blades. In the example shown, the shaft 316 and the first blade 314 are integral. In alternative examples, the shaft 316 and the first blade 314 may be separate pieces that are mounted or secured together.

In the example shown, the shaft 316 extends along a shaft longitudinal axis 318, which in use defines an axis of rotation of the impeller 304, and is coincident with the longitudinal axis 306 of the holding vessel 302. A motor 320 (shown in FIG. 2) drives rotation of the shaft 316 about the axis 318, which drives rotation of the impeller 304 about the axis 318.

Referring still to FIGS. 3A to 3C, the first blade 314 defines a plane of rotation 322. In the example shown, the first blade 314 is generally cylindrical, and includes a leading portion 328, and a trailing portion 330. The leading portion 328 defines the plane of rotation 322.

In alternative examples, the first blade may be another shape other than cylindrical. For example (not shown), the first blade may be generally planar, and have a top surface, a bottom surface, a leading edge, and a trailing edge. In such examples, the first blade (i.e. the top and bottom surfaces) may be generally perpendicular to the plane of rotation, or exactly perpendicular to the plane of rotation.

As used herein the term "generally perpendicular" includes orientations of between 80 degrees and 100 degrees. The term "exactly perpendicular" refers to orientations of 90 degrees. Similarly, the term "generally parallel" includes orientations of between −10 degrees and 10 degrees. The term "exactly parallel" refers to orientations of 0 degrees. Further, the term "generally non-perpendicular" includes any orientation that is not between 80 degrees and 100 degrees, and the term "generally non-parallel" includes any orientation that is not between −10 degrees and 10 degrees.

Referring still to FIGS. 3A to 3C, in the example shown, the first blade 314 is generally non-parallel and generally non-perpendicular to the shaft longitudinal axis 318. In other words, the first blade 314 is inclined with respect to the axis 318, as shown by angle 334 in FIG. 3A. This facilitates rotational flow throughout the depth of the suspension 202.

Referring back to FIG. 2, in the example shown, in order to further facilitate rotational flow while inhibiting axial and radial flow, the holding vessel 302 is generally circular in cross section, and is not provided with any baffles or other structures that are commonly used in the art to promote mixing.

In the example shown, in use, the suspension 202 is supplied to the holding vessel 302 from the singulation module 200, via conduit 206 and valve 208. The impeller 304 is immersed in the suspension 202, and the suspension 202 is stirred by rotation of the impeller 304 about the axes 306, 318. Due to the configuration of the impeller 304, the rotation of the impeller 304 induces rotational flow in the holding vessel 302, while inhibiting radial flow and axial flow. In addition, the impeller 304 may be rotated generally slowly, at a speed selected to avoid the formation of a vortex in the holding vessel 302. This flow pattern may maintain the embryos 102 in suspension (i.e. prevent, minimize, or inhibit clumping or settling of the embryos 102), while preventing, minimizing, or inhibiting damage to the embryos 102 (e.g. damage that might be caused by fast and/or turbulent flow and/or high speed impact with an impeller).

Referring back to FIGS. 1A and 1B, from the holding module 300, the suspension 202 is supplied to the pick-and-place module 400, and more specifically, is metered into the pick-and-place module 400, as will be described below. In the example shown, the suspension 202 flows from the holding module 300 through an outlet conduit 336, under the force of gravity.

As mentioned above, the pick-and-place module 400 includes a preparation module 500, an identification module 600, and a handling module 700. As will be described in further detail below, the preparation module 500 receives the suspension 202 from the holding vessel 302, and meters and spreads the suspension 202 so that the embryos 102 in the suspension 202 are spaced apart and prepared for identification. The identification module 600 identifies target plant embryos 102a amongst the prepared embryos 102. For example, the identification module 600 may identify target plant embryos 102a based on size. The handling module 700 picks the target plant embryos 102a out of the suspension 202, and deposits the target plant embryos 102a at a target location 800.

Figure 4A:
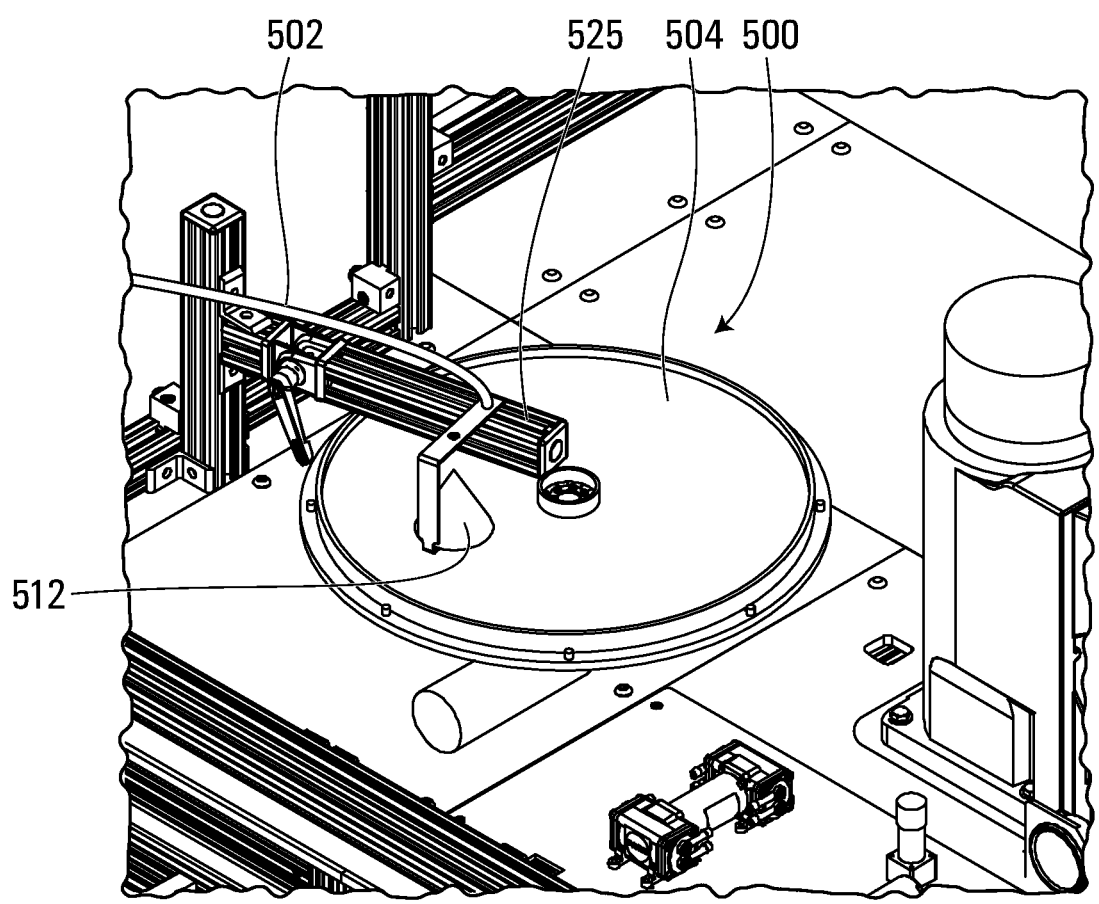
FIG. 4A is a perspective view of the preparation module of FIG. 1A.
Figure 4B:
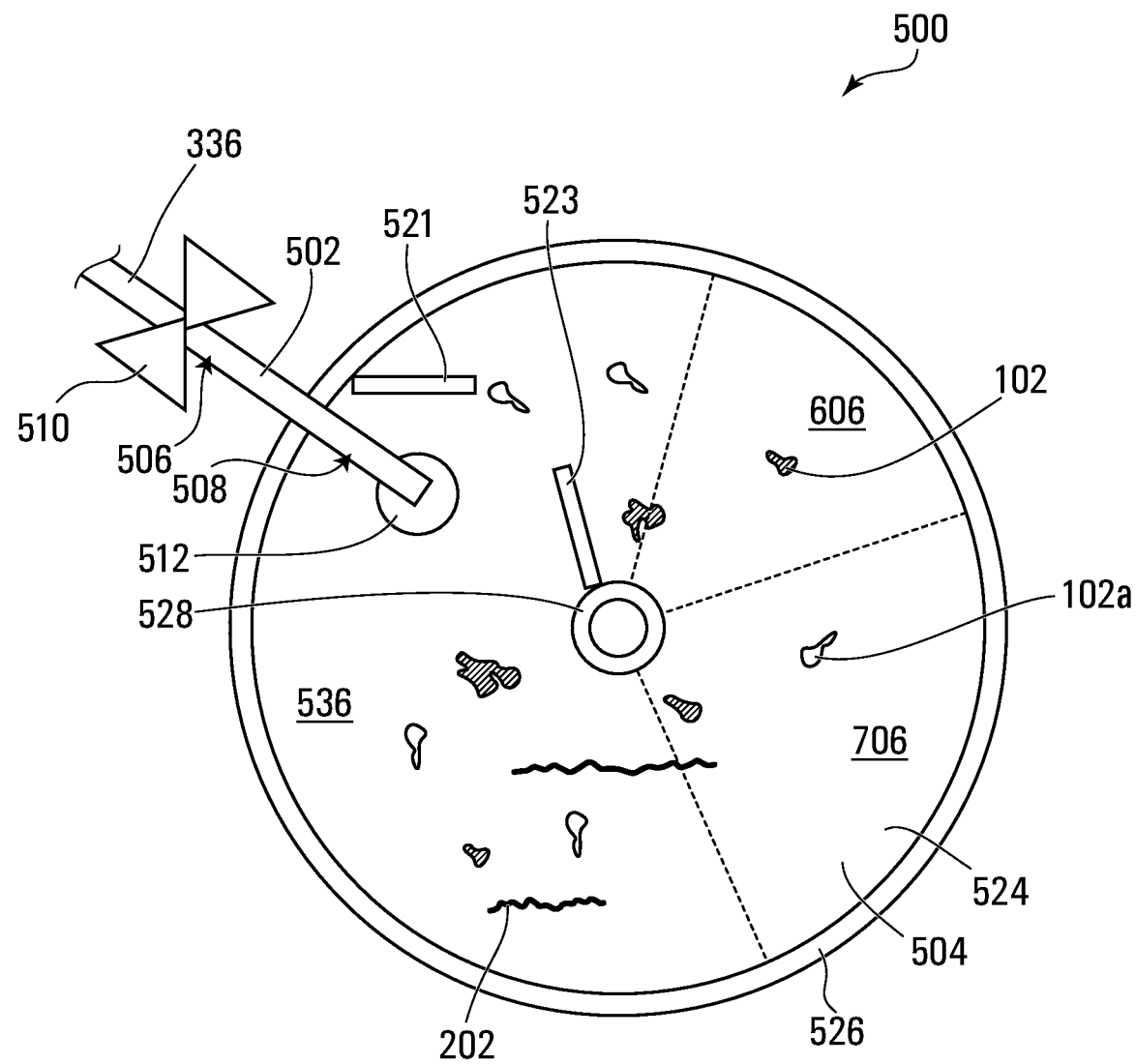
FIG. 4B is a top view of the preparation module of FIG. 4A.
Figure 4C:
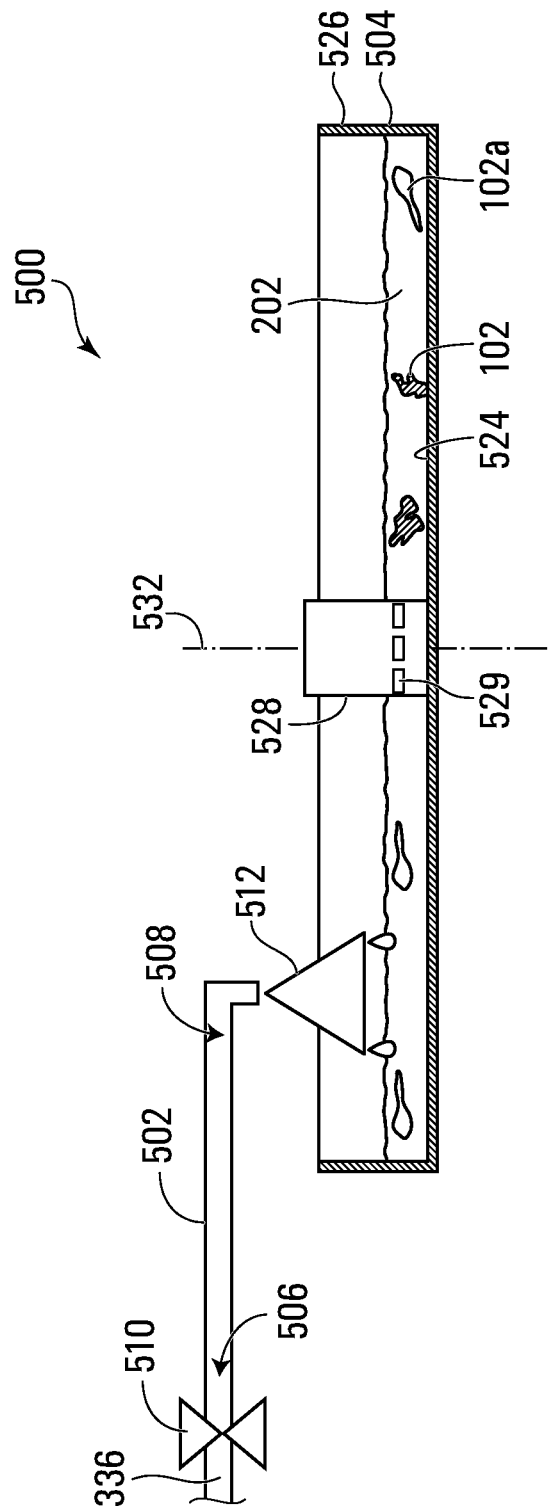
FIG. 4C is a side view of the preparation module of FIG. 4A.

Referring now to FIGS. 4A to 4C, in the example shown, the preparation module 500 includes an inlet conduit 502 and a tray 504. The inlet conduit 502 has an inlet end portion 506 for receiving the suspension 202 and an outlet end portion 508 for depositing the suspension 202 into the tray 504.

In the example shown, the inlet end portion 506 is in communication with the outlet conduit 336 of the holding module 300 via a valve 510 (e.g. a pinch valve), which meters the suspension 202 into the pick-and-place module 400. As will be described below, in the example shown, the valve 510 is in communication with the identification module 600, and is configured to open based on a signal from the identification module 600. For example, the identification module 600 may determine that the number of embryos 102 in the pick-and-place module 400 is below a minimum value, and send a signal to open the valve 510.

Figure 5B:
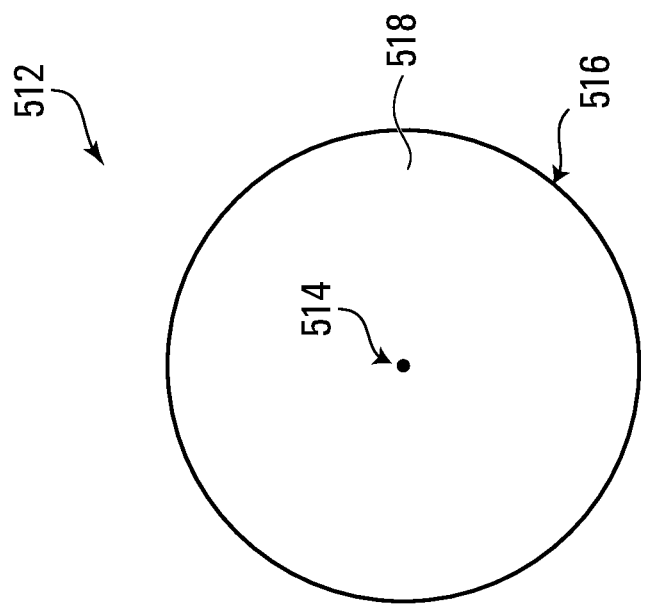
FIG. 5B is a top view of the dispersion element of FIG. 5A.
Figure 5A:
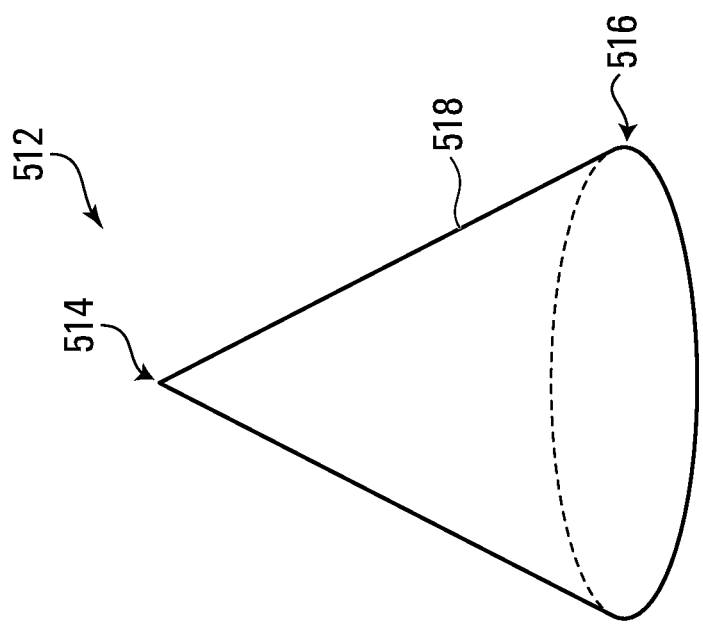
FIG. 5A is a perspective view of the dispersion element of the preparation module of FIG. 4A.

Referring also to FIGS. 5A and 5B, in the example shown, the outlet end portion 508 of the conduit 502 includes a dispersion element 512 for spreading out the suspension 202 as the suspension 202 is deposited into the tray 504. In the example shown, the dispersion element 512 is generally conical. More specifically, the dispersion element 512 has an upstream end 514 spaced from the tray 504, and a downstream end 516 adjacent the tray 504. A sidewall 518 extends between the upstream end 514 and the downstream end 516. The cross-sectional area of the sidewall 518 increases from the upstream end 514 to the downstream end 516, so that the sidewall 518 is flared and generally conical. The sidewall 518 is in fluid communication with the inlet end portion 506 of the inlet conduit 502 and also with the tray 504, so that the suspension 202 is deposited onto and flows along the sidewall 518 as it passes into the tray 504. Because the sidewall 518 is flared, drops of the suspension land at different locations as they land in the tray 504.

Referring back to FIGS. 4A to 4C, as noted above, the tray 504 receives the suspension 202 from the inlet conduit 502. The tray can hold the suspension, i.e. the tray is non-porous and non-liquid permeable. In the example shown, the tray 504 is generally circular (when viewed from above), and has a base surface 524, an outer rim 526 extending upwardly from the base surface 524 around a periphery of the base surface 524, and an inner rim 528 positioned radially inwardly from the outer rim 526 and extending upwardly from the base surface 524. The base surface 524 is generally annular, and extends between the inner rim 528 and the outer rim 526.

In the example shown, the inner rim 528 defines a centrally positioned drain of the tray 504. Perforations 529 (shown in FIG. 4C) in the inner rim allow for fluid to drain via the inner rim 528.

The tray 504 further has a central axis 532, which extends perpendicularly to the base surface 524.

The tray 504 is movable. In the example shown, the tray 504 is movable with respect to the outlet end portion 508 of the inlet conduit 502, to further disperse the suspension 202 around the tray 504 as the suspension 202 is deposited into the tray 504. The tray is also movable with respect to the identification module 600 and handling module 700, to repeatedly reposition the plant embryos 102 in the tray 504 with respect to the identification module 600 and handling module 700. As will be described below, the tray 504 can be moved while the suspension is deposited into the tray 504, while the identification module 600 identifies target plant embryos 102a amongst the embryos 102 in the suspension 202, and/or while the handling module 700 picks the target plant embryos 102a out of the suspension 202. Alternatively, the tray can stop moving while the suspension is deposited into the tray 504, while the identification module 600 identifies target plant embryos 102a amongst the embryos 102 in the suspension 202, and/or while the handling module 700 picks the target plant embryos 102a out of the suspension 202. In the example shown, the tray 504 is movable by rotation about the central axis 532.

In the example shown, rotation of the tray 504 is driven by a motor 534 (shown in FIG. 1B). Rotation of the tray 504 may be generally smooth and slow. For example, the tray 504 may be rotated at a speed of between about 1 revolution in 20 minutes and about 1 revolution in 5 minutes, or between about 1 revolution in 15 minutes and about 1 revolution in 10 minutes. Slow and smooth rotation of the tray 504 may allow for the embryos 102 to rotate with the tray 504, and therefore move with respect to the identification module 600 and handling module 700, while minimizing or inhibiting movement of the embryos 102 with respect to the tray 504. For example slow and smooth rotation may minimize the formation of waves or currents which may cause the embryos 102 to move within the tray 504.

Referring to FIGS. 4B and 4C, in operation, at startup, the tray 504 may be supplied with suspension 202 from the holding module 300 via the outlet conduit 336, the valve 510, and the inlet conduit 502. The tray 504 may be supplied with suspension 202 until, for example, the level of suspension 202 in the tray 504 is at or near the top of the inner rim 528. At steady state, as the tray 504 is rotated about the central axis 532, target embryos 102a in the suspension 202 may be identified by the identification module 600 and removed from the tray 504 by the handling module 700, as will be described in detail below. Furthermore, as the tray 504 is rotated, additional suspension 202 may be metered into the tray 504 by the valve 510, via the inlet conduit 502 and dispersion element 512, to replenish the tray 504 with embryos 102. The additional suspension 202 may be slowly metered into the tray 504. For example, the additional suspension 202 may be metered into the tray 504 in a dropwise fashion. This may minimize disturbances to the suspension 202 in the tray 504. Due to the rotation of the tray 504 and the use of the dispersion element 512, the additional suspension 202 is spread and dispersed around the tray 504 as the suspension 202 is deposited, and the embryos 102 are spaced apart in the tray 504. As additional suspension is slowly deposited into the tray 504, the suspension 202 already in the tray 504 may slowly drain from the tray 504 via the inner rim 528. As such, both liquid and embryos can be continually supplied to the tray 504 (via the addition of new suspension 202) and continually removed from the tray 504 (via the draining of suspension via the inner rim 528 and the removal of target embryos 102a), to maintain steady state conditions and continuous operation.

In the example shown, the preparation module 500 further includes a pair of flow guides 521, 523 (shown in FIG. 4B). The flow guides as well as the inlet conduit 502 may be supported by a support member 525 (shown in FIG. 4A). The first flow guide 521 may be positioned adjacent the outer rim 526, and the second flow guide 523 may be positioned adjacent the inner rim 528. The flow guides 521, 523 may direct the suspension in the tray 504 away from the outer rim 526 and the inner rim 528, so that the embryos are accessible to the identification 600 and handling 700 modules.

Referring back to FIG. 1B, in the example shown, the identification module 600 is configured to identify target plant embryos 102a (also referred to herein as "target embryos") amongst the embryos 102 in the suspension 202 in the tray 504 (e.g. identify embryos of a certain size), optionally while the tray is moving, and the handling module 700 is configured to pick the target plant embryos 102a out of the suspension 202 in the tray 504, optionally while the tray is moving, and deposit the target plant embryos 102a at a target location 800 (e.g. a storage tray). The identification module 600 and the handling module 700 are in communication, so that handling module 700 picks up the embryos identified as target embryos 102a by the identification system 600. The identification module 600 and handling module 700 may be referred to collectively as an "identification and handling module".

Figure 6:
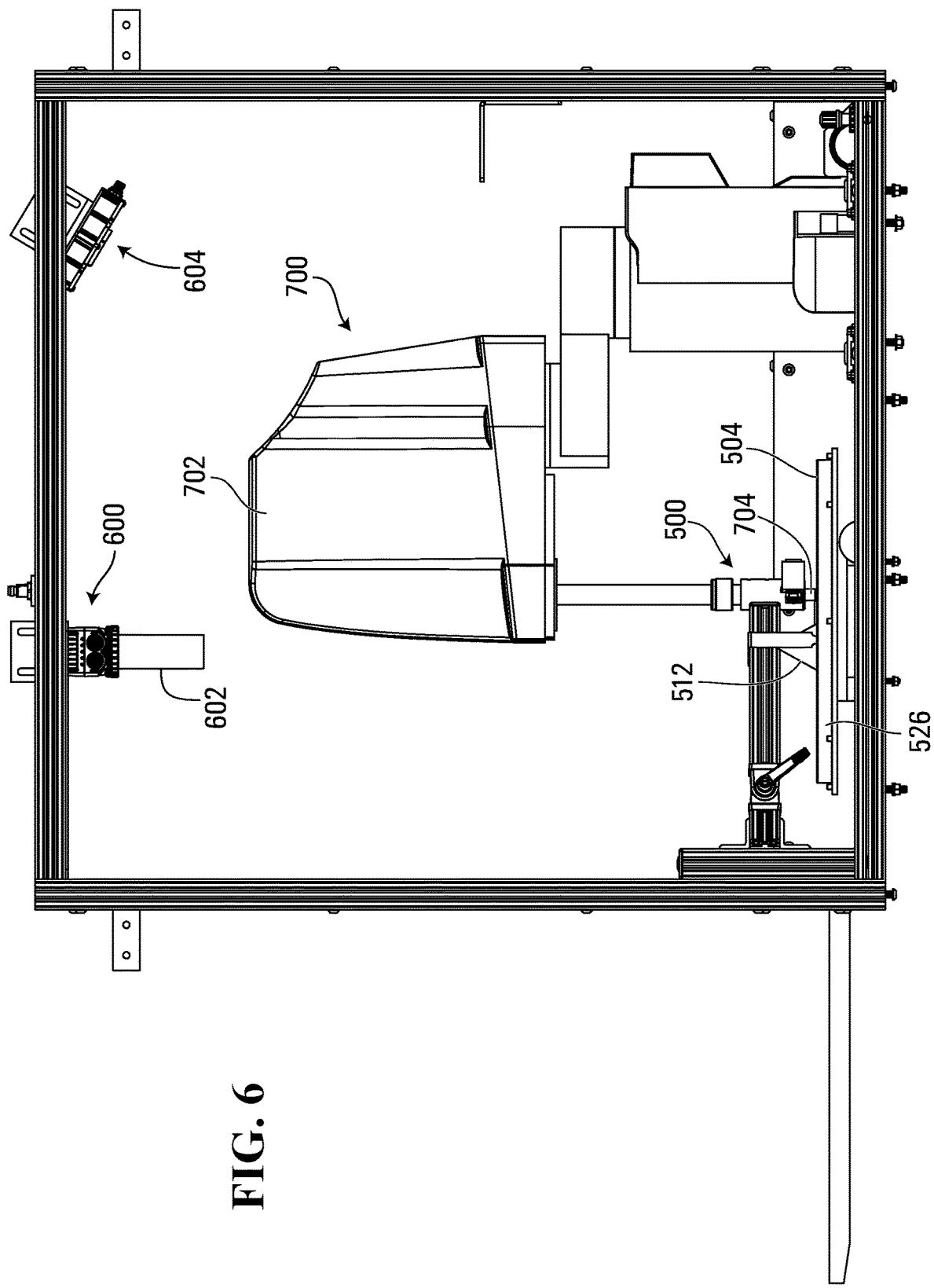
FIG. 6 is a side view of the pick-and-place module of FIG. 1A, including the preparation module of FIGS. 4A to 4C, an identification module, and a handling module.

Referring now to FIG. 6, in the example shown, the identification system 600 is proximate the tray 504, and includes a camera 602 and an image processing system (not shown) connected to the camera 602. The image processing system may be part of a control system of overall system 100.

In the example shown, the camera 602 is stationary, and is positioned and configured to capture images of the plant embryos 102 in the suspension 202 in the tray 504 as the tray 504 is rotated and the plant embryos 102 in the tray 504 pass into the main field of view of the camera 602.

The image processing system is configured to analyze the images captured by the camera 602, and identify target plant embryos 102a amongst the imaged embryos 102. For example, the image processing system may analyze the images to determine at least one parameter of the imaged embryos 102 from the image. For example, the image processing system may determine the size of the imaged embryos 102, and any of the imaged embryos 102 that are of a desired size may then be identified as target plant embryos 102a. For example, healthy and fully separated embryos may be within a particular size range, and the image processing system may be configured to identify embryos within this size range as target plant embryos 102a. On the other hand, underdeveloped embryos may be smaller than this size range and clumped embryos may be larger than this size range, and would not be identified as target plant embryos 102a. In some examples, the size of the imaged embryos may be determined based on the pixel intensity of the imaged embryos. The image processing system may score and rank each imaged embryo based on pixel intensity. The image processing system may then identify the imaged embryo(s) of the highest pixel intensity as target embryos. In addition, the image processing system may identify whether any target embryos are too close to any other embryos, so that the handling module does not pick up more than one target embryo at a time.

Referring still to FIG. 6, in the example shown, in order to facilitate the identification of target plant embryos 102a, the identification system 600 further includes a light 604 positioned to illuminate the plant embryos 102 in the suspension 202 in the tray 504. In some examples the light 604 may illuminate the embryos 102 with a colored light such as green light. It has been determined that the use of green light may allow for more accurate identification of target embryos 102a. In order to further accelerate contrast and facilitate the identification of target plant embryos 102a, the tray 504 may be relatively dark in color, such as black in color.

Referring still to FIG. 6 and also to FIGS. 1A and 1B, the handling module 700 includes a robotic arm 702 proximate the tray 504. In the example shown, upon identification of a target plant embryo 102a by the identification module 600, the robotic arm 702 is actuated to pick the target plant embryo 102a out of the suspension 202 in the tray 504 while the tray is moving, and deposit the target plant embryo 102a at a target location 800. For example, as will be described in further detail, the robotic arm 702 includes a tip 704 for handling the embryos. The robotic arm 702 and the tip 704 are configured to handle one target embryo 102a at a time. When the identification module 600 identifies a target plant embryo 102a amongst the plant embryos 102 in the tray 504, the robotic arm 702 is actuated so that the tip 704 is moved towards the target plant embryo 102a, picks up the target plant embryo 102a, and transfers the target plant embryo 102a to the target location 800. This can be repeated continuously as the identification system 600 identifies target plant embryos 102a. In the example shown, the identification system 600 is in communication with the robotic arm 702, and actuation of the robotic arm 702 is automatic (e.g. based on a signal received from the image processing system).

Referring back to FIG. 4B, in the example shown, embryos 102 in the tray 504 rotate through three zones, the boundaries of which are shown by dotted line: a monitoring zone 606, which is in the main field of view of the camera 602, and where the quantity of embryos is monitored by the identification module, so that if the quantity of embryos in the tray 504 becomes low, a signal can be sent to the holding module to call for more embryos; an identification and handling zone 706, which is downstream of the monitoring zone 606, in the main field of view of the camera 602, and within the reach of the robotic arm 702, and where the target embryos 102a are located when they are imaged, identified, and picked up; and an addition zone 536, where the suspension 202 is deposited into the tray 504 by the dispersion element 512, and where embryos 102 may be out of the main field of view of the camera 602 and out of reach of the robotic arm 702.

In use, as the tray 504 is rotated, embryos 102 are deposited into the tray 504 in the addition zone 536. As the tray 504 rotates, the embryos rotate into the monitoring zone 606, where they are imaged by the camera so that the quantity of embryos can be monitored. As the tray 504 continues to rotate, the embryos pass from the monitoring zone 606 into the identification and handling zone 706. In the identification and handling zone 706, the embryos 102 are imaged by the camera 602, and target plant embryos 102a are identified. Also in the identification and handling zone 706, the target plant embryos 102a identified by the identification module 600 are picked up by the robotic arm 702, and transferred to a target location 800 (shown in FIG. 1B). The robotic arm 702 then returns to the identification and handling zone 706 to pick up a subsequent target plant embryo 102a. As this process continues and as the robotic arm 702 picks up target embryos 102a within the identification and handling zone 706, some target embryos 102a may pass out of the identification and handling zone 706 and back into the addition zone 536, before they are picked up by the robotic arm 702. As the tray 504 continues to rotate, these missed target embryos 102a will pass back into the monitoring zone 606 and then back into the identification and handling zone 706, and will have another opportunity to be identified and picked up. Some target embryos 102a may pass out of and back into the monitoring 606 and identification and handling 706 zones numerous times before being picked up by the robotic arm 702. Alternatively, some target embryos 102a will be picked up by the robotic arm 702 on their first pass through the monitoring zone 606 and identification and handling 706 zones.

On the other hand, non-target embryos (e.g. embryos that are not of a certain size) will repeatedly rotate through the monitoring zone 606, identification and handling zone 706, and addition zone 536, without being picked up. As mentioned above, as the target embryos 102a are picked up, additional suspension 202 is deposited into the tray 504, and suspension 202 within the tray 504 drains via the inner rim 528. Over time, as the tray 504 rotates and the suspension 202 drains, the non-target embryos will move towards the inner rim 528, and will eventually also drain from the tray 504 via the inner rim 528.

Turning now to FIGS. 7A to 7E, an example of the motion of the robotic arm 702 will be described. In the example shown, the first target location 800 is a receiving plate 802 (shown in FIG. 7E), which is adjacent the singulation module 400. Several receiving plates 802 are provided, and the receiving plates 802 are movable along a plate conveyor 804. After the first receiving plate 802 receives one or more target embryos 102a, it may be moved along the plate conveyor 804, for example to a secondary storage area (not shown), and a subsequent receiving plate 802 may take its place so that the subsequent receiving plate 802 may receive the next target embryo from the handling module 700. The receiving plates 802 may contain, for example, a growth media in a semi-solid gelling agent.

Figure 7A:
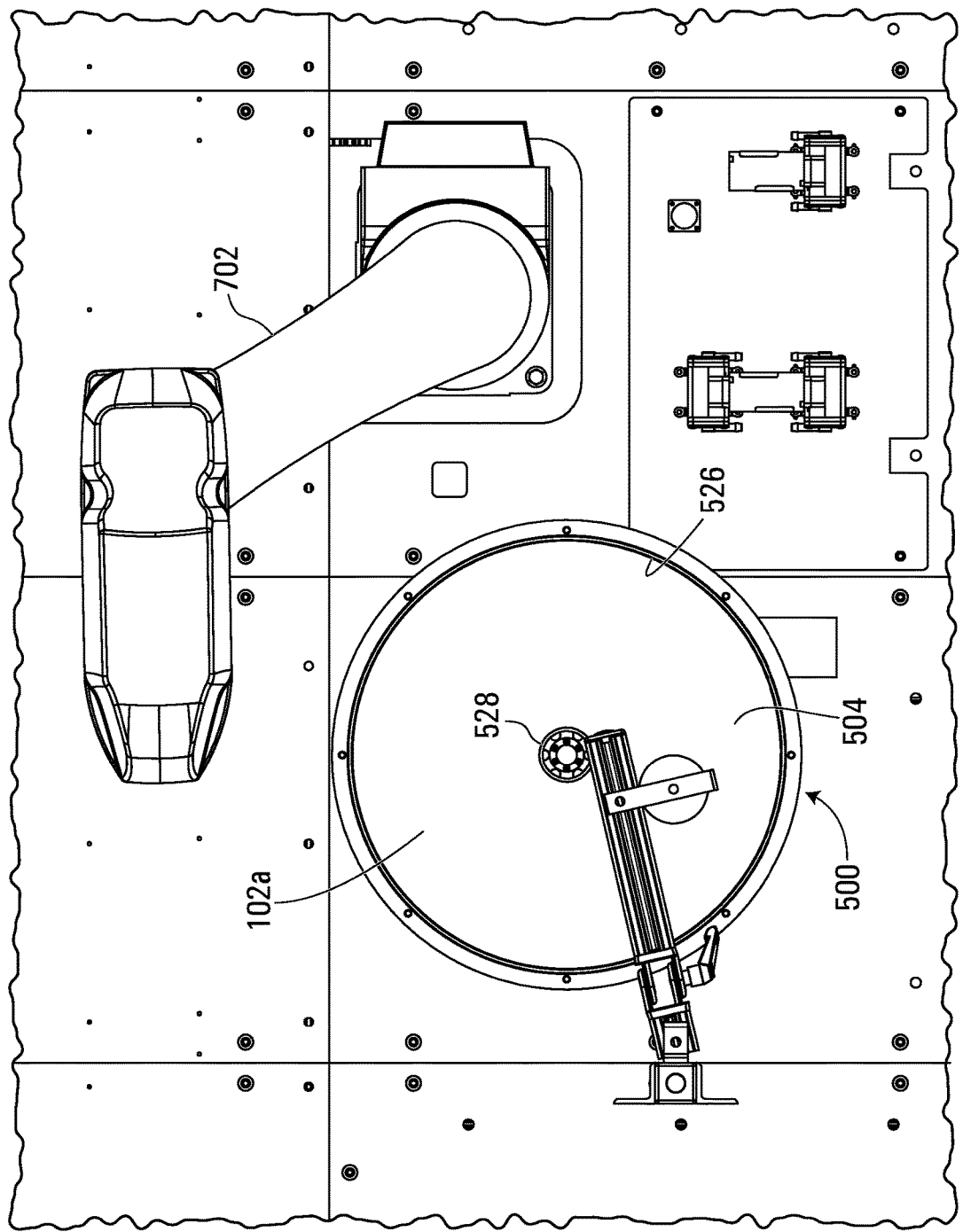
FIG. 7A is a top view of the pick-and-place module of FIG. 1A, with the robotic arm in a neutral position.
Figure 7B:
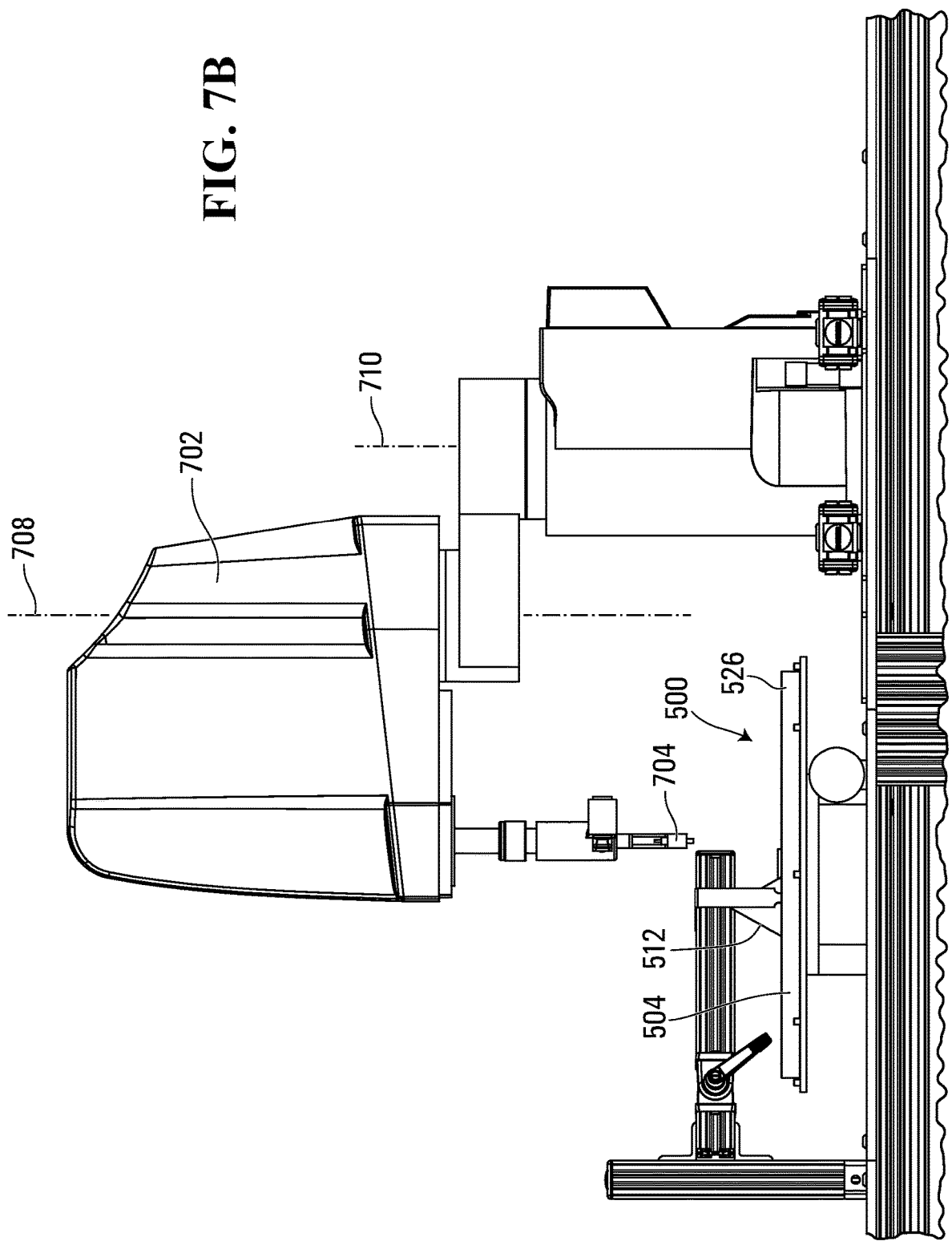
FIG. 7B is a side view of the pick-and-place module of FIG. 1A, with the robotic arm in the neutral position.
Figure 7C:
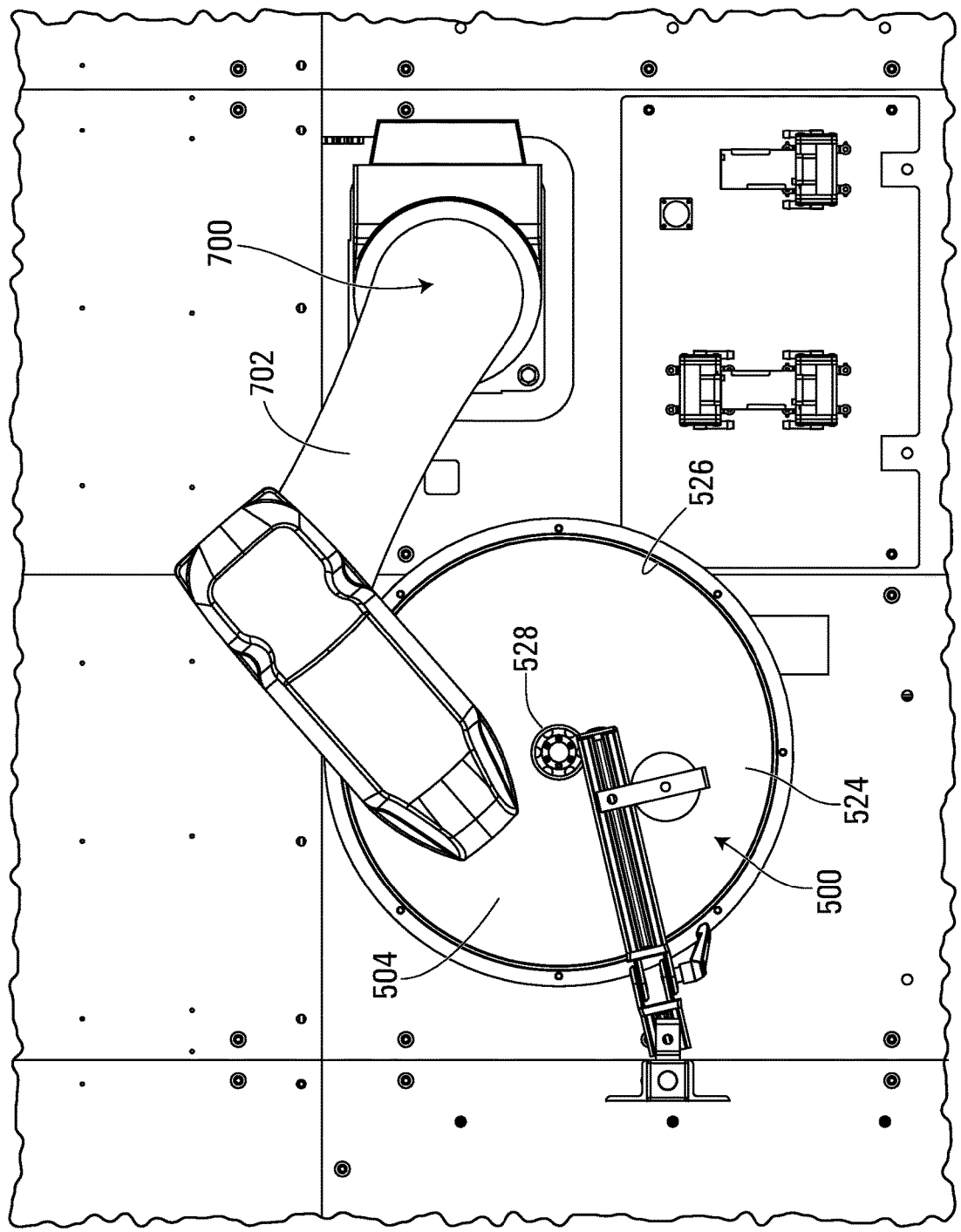
FIG. 7C is a top view of the pick-and-place module of FIG. 1A, with the robotic arm in position to pick up a target plant embryo.
Figure 7E:
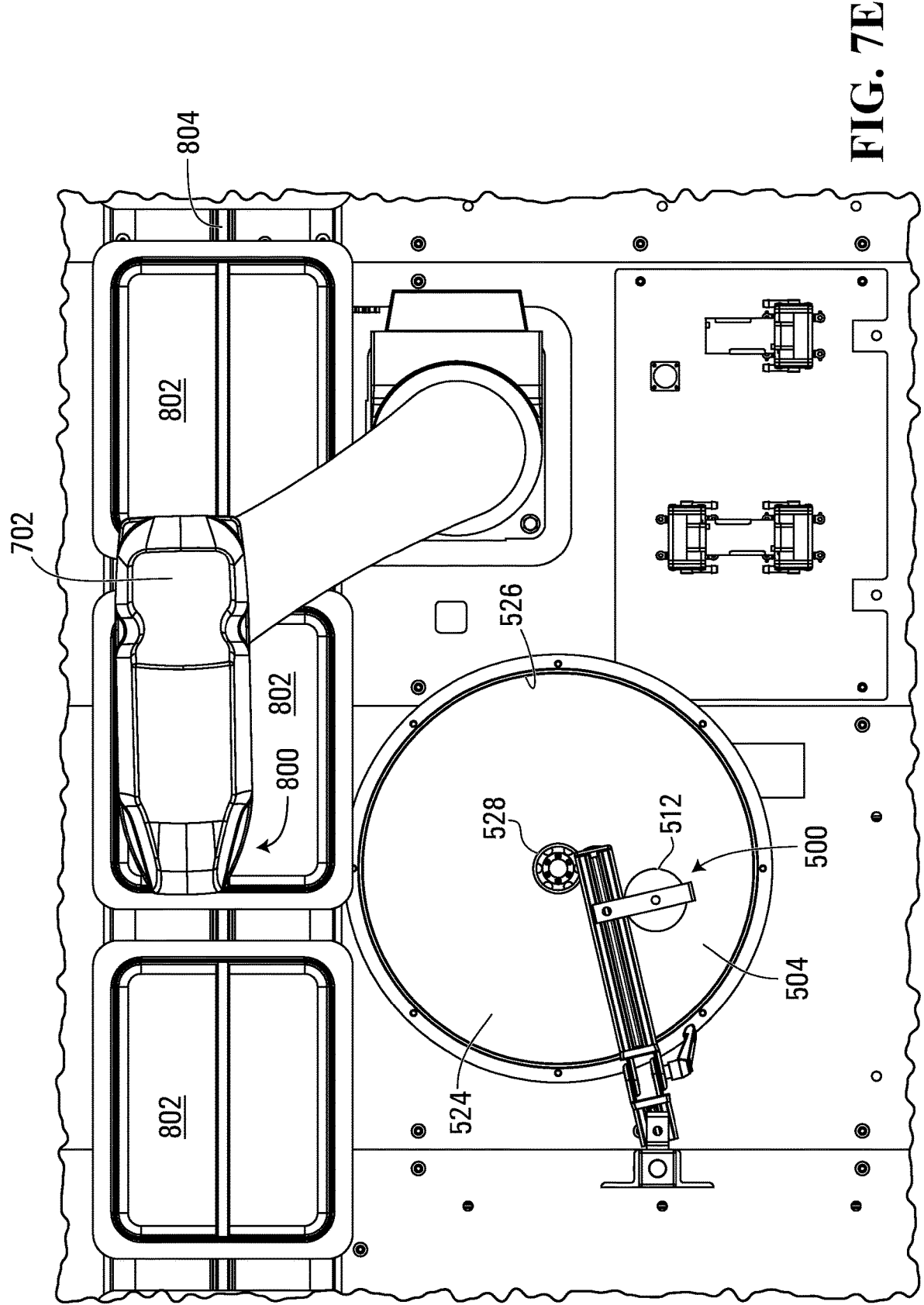
FIG. 7E is a top view of the pick-and-place module of FIG. 1A, with the robotic arm in position to deposit a target plant embryo at a target location.

Referring to FIGS. 7A and 7B, the robotic arm 702 is shown in a neutral position. When the identification module 600 (not shown in FIGS. 7A to 7E) identifies a target plant embryo 102a in the tray 504, the robotic arm is actuated to move the tip 704 both horizontally towards the tray and vertically downwardly, towards the target plant embryo 102a, as shown in FIGS. 7C and 7D. The tip 704 may then pick up the target plant embryo 102a (as will be described in further detail below). When the target plant embryo 102a has been picked up, the robotic arm 702 is actuated to move the tip 704 vertically upwardly, so as to clear the outer rim 526 of the tray 504, and horizontally from the tray 504 towards one of the receiving plates 802, as shown in FIG. 7E. The robotic arm 702 is then actuated to move the tip 704 downwardly towards the receiving plate 802, to deposit the target plant embryo 102a on the receiving plate 802. The robotic arm can then be actuated to move the tip 704 back towards the tray 504, to pick up a subsequent target plant embryo 102a identified by the identification module 600.

As can be seen in FIGS. 7B and 7D horizontal movement of the tip 704 is effected by rotation of tip 704 about a first generally vertical robot axis 708 and a second generally vertical robot axis 710. Furthermore, in the example shown, vertical movement of the tip 704 is effected by linear sliding motion of the tip 704. In other examples, movement of the tip 704 may be effected in another manner. For example, horizontal movement may be effected by linear sliding.

The combination of holding module 300, preparation module 500, identification module 600, and handling module 700 as described above may allow for singulated plant embryos to be maintained in suspension while awaiting transfer to a target location. In other words, in the example described above, the embryos are not dried, and are not removed from suspension until they are transferred. This may promote embryo health.

Referring now to FIGS. 8A to 8C, the tip 704 is shown in greater detail. For illustrative purposes a target plant embryo 102*a* is shown held to the tip in FIG. 8C.

In the example shown, the tip 704 picks up and deposits the target embryos 102*a* by suction and blowing, respectively. More specifically, the tip 704 applies a suction force to draw a target plant embryo 102*a* towards the tip 704, and applies a blowing force to release the target plant embryo 102*a* from the tip 704.

Referring still to FIGS. 8A to 8C, in the example shown, the tip 704 includes a body 712 extending along a body axis 714. The body has a body proximal portion 716 defining a body proximal end 718, and a body distal portion 720 defining a body distal end 722. The body proximal portion 716 is mountable to the robotic arm 702, and the body distal portion 720 handles embryos.

Referring to FIG. 8C, in the example shown, a bore 724 extends into the body 712 from the body distal end 722. The bore 724 has a bore distal end 726 at the body distal end 722, and an opposed bore proximal end 728. The bore 724 has a bore cross-sectional area transverse to the body axis 714.

Referring still to FIG. 8C, in the example shown, a conduit 730 is in fluid communication with the bore 724, and extends proximally from the bore 724 and through the body 712, along the body axis 714. The conduit 730 is connectable to a source of air (e.g. a diaphragm pump, not shown), to provide suction and blowing forces. The conduit 730 has a conduit cross-sectional area transverse to the body axis 714.

Referring still to FIG. 8C, in the example shown, the conduit cross-sectional area is less than the bore cross-sectional area. For example, the diameter of the bore (also referred to as the "bore diameter") may be between 1.5 and 4 times the diameter of the conduit (also referred to as the "conduit diameter"), or between 2.0 and 2.5 times the conduit diameter. For example, the bore diameter area may be between 3 mm and 4 mm, and the conduit diameter may be between 1 mm and 2 mm.

Referring to FIGS. 8A to 8C, a screen 732 extends across the bore 724. The screen 732 receives and holds plant embryos 102 that are suctioned towards the conduit 730, and generally prevents plant embryos from being suctioned into the conduit 730. In the example shown, the screen 732 is positioned at the bore distal end 726, and is secured to the body distal end 722. In alternative examples, the screen 732 may be nested within the bore 724, for example at the bore proximal end 728. The screen 732 may be secured to body 712 for example by an adhesive or a mechanical fastener.

Referring to FIG. 8C, in the example shown, the body 712 includes a tapered shoulder 734 at a junction of the bore 724 and the conduit 730. In alternative examples, the shoulder may be square.

Referring still to FIG. 8B, in the example shown, the body 712 has a wall thickness 736 around the bore 724 that is relatively small, for example between about 0.25 mm and about 1.25 mm, or between about 0.5 mm and about 1.0 mm. This relatively small wall thickness 736 may prevent, minimize, or inhibit plant embryos from sticking to the body distal end. The wall thickness 738 (shown in FIG. 8C) around the conduit 730 may be the same as or different from the wall thickness 736 around the bore 724.

In use, when suction is applied to the conduit 730, the suction may draw a target plant embryo 102*a* towards the screen 732, and cause the target plant embryo 102*a* to be held to the screen 732. The target plant embryo 102*a* may then be moved to the target location 800 by actuation of the robotic arm 702. When the target plant embryo 102*a* is at the target location 800, the target plant embryo 102*a* may be released from the screen 732 by stopping the suction force or reversing the suction force (i.e. applying a blowing force).

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

The invention claimed is:

1. A pick-and-place method for plant embryos, comprising:
  a) flowing a suspension of singulated plant embryos into a tray while moving the tray;
  b) moving the tray;
  c) while moving the tray, identifying a target plant embryo amongst the plant embryos in the suspension in the tray using an identification system proximate the tray;
  d) after step c) and while moving the tray, picking the target plant embryo out of the suspension in the tray using a robotic arm proximate the tray and in communication with the identification system, the robotic arm actuatable to pick the target plant embryo out of the suspension in the tray while the tray is moving; and
  after step d), the robotic arm depositing the target plant embryo at a target location,
wherein the moving the tray comprises rotating the tray and wherein the tray comprises a base surface and central axis that is perpendicular to the base surface, and the tray is movable by rotation about the central axis, wherein the tray further comprises an outer rim extending upwardly from the base surface and around a periphery of the base surface, and an inner rim extending upwardly from the base surface, whereby the base surface is annular and extends between the inner rim and the outer rim, and the outer rim is taller than the inner rim, and the inner rim defines a drain of the tray.

2. The method of claim 1, wherein the suspension of singulated plant embryos are maintained in suspension by:
  a) supplying the suspension of the plant embryos in a liquid to a holding vessel;
  b) immersing a rotational flow impeller in the suspension, the rotational flow impeller having at least a first blade, wherein the first blade defines a plane of rotation; and
  c) stirring the suspension by rotating the rotational flow impeller about a generally vertical axis of rotation.

3. The method of claim 1, comprising flowing the suspension along a dispersion element into the tray, wherein:

i) the dispersion element comprises an upstream end spaced from the tray, a downstream end adjacent the tray, and a sidewall extending between the upstream end and downstream end;

ii) a cross-sectional area of the sidewall increases from the upstream end to the downstream end; and iii) step a) comprises flowing the suspension of plant embryos along the sidewall, preferably wherein the sidewall is conical.

4. The method of claim 1, wherein step c) comprises identifying the target plant embryo based on size.

5. The method of claim 4, wherein step c) further comprises illuminating the suspension in the tray with a colored light.

6. The method of claim 4, wherein step c) comprises:

i) capturing images of the plant embryos in the suspension in the tray;

ii) analyzing the images; and iii) identifying the target plant embryo based on the images.

7. The method of claim 1, wherein step d) comprises actuating the robotic arm to pick the target plant embryo out of the suspension, the robotic arm having a tip for handling the target plant embryo, and applying a suction force to the tip to draw the target plant embryo towards the tip.

8. The method of claim 7, further comprises step e) wherein step e) comprises actuating the robotic arm to move the target plant embryo to the target location and applying a blowing force to release the target plant embryo from the tip.

9. The method of claim 7, wherein:

i) the tip comprises a conduit in fluid communication with a source of suction, and a screen upstream of the conduit and in fluid communication with the conduit;

ii) step d) comprises suctioning the target plant embryo onto the screen, and step e) comprises blowing the target plant embryo off of the screen.

10. The method of claim 2, wherein the first blade is generally perpendicular to the plane of rotation and step c) comprises inducing rotational flow in the holding vessel, wherein radial flow and/or axial flow are inhibited.

11. The method of claim 2, further comprising rotating the rotational flow impeller at a speed selected to avoid the formation of a vortex in the holding vessel.

12. The method of claim 5, wherein the coloured light is a green light.

13. A pick-and-place system for plant embryos, comprising:

a) a tray for receiving a suspension of plant embryos, wherein the tray is movable to repeatedly reposition the plant embryos, wherein the tray comprises a base surface and central axis that is perpendicular to the base surface, and the tray is movable by rotation about the central axis, wherein the tray further comprises an outer rim extending upwardly from the base surface and around a periphery of the base surface, and an inner rim extending upwardly from the base surface, whereby the base surface is annular and extends between the inner rim and the outer rim, and the outer rim is taller than the inner rim, and the inner rim defines a drain of the tray;

b) an identification system proximate the tray for identifying a target plant embryo amongst the plant embryos in the suspension in the tray, wherein the identification system is configured to identify the target plant embryo while the tray is moving; and c) a robotic arm proximate the tray and in communication with the identification system, the robotic arm actuatable to pick the target plant embryo out of the suspension in the tray while the tray is moving, and deposit the target plant embryo at a target location.

14. The system of claim 13, wherein the system further, comprises:

a) a holding vessel;

b) a rotational flow impeller the rotational flow impeller rotatable about a generally vertical axis of rotation, the rotation flow impeller having at least a first blade, wherein the first blade defines a plane of rotation wherein the holding vessel and the rotational flow impellar are for maintaining separated plant embryos in suspension.

15. The system of claim 13, wherein the identification system comprises a camera and an image processing system connected to the camera, the camera positioned to capture images of the plant embryos in the suspension as the tray is moved, and the image processing system configured to analyze the images and identify the target plant embryo amongst the plant embryos in the suspension, wherein the image processing system is configured to determine at least one parameter of the plant embryos.

16. The system of claim 15, wherein the identification system further comprises a light positioned to illuminate the plant embryos in the suspension in the tray.

17. The system of claim 13, wherein the robotic arm comprises a tip for handling the target plant embryo, and is actuatable to move the tip horizontally between the tray and the target location, and downwardly towards the tray to pick the target plant embryo out of the suspension, wherein the tip is configured to apply suction to draw the target plant embryo towards the tip, configured to apply a blowing force to release the target plant embryo from the tip.

18. The system of claim 17, wherein the tip comprises:

i) a screen for holding the first target plant embryo; and ii) a conduit between the screen and a source of suction for suctioning the target plant embryo onto the screen.

19. The system of claim 13, further comprising a conduit for depositing the suspension of plant embryos into the tray, the conduit having an inlet end portion for receiving the suspension of plant embryos and an outlet end portion for dispensing the suspension of plant embryos into the tray; wherein the tray is movable with respect to the outlet end portion to spread the suspension as the suspension is deposited into the tray.

20. The system of claim 19, wherein the outlet end portion of the conduit comprises a dispersion element for further spreading the suspension as the suspension is deposited into the tray, and:

i) the dispersion element comprises an upstream end spaced from the tray, a downstream end adjacent the tray, and a sidewall extending therebetween; and ii) a cross-sectional area of the sidewall increases from the upstream end to the downstream end.

21. The system of claim 14, wherein the first blade is generally perpendicular to the plane of rotation, generally non-parallel to the axis of rotation, generally non-perpendicular to the axis of rotation, and the shaft extends along the axis of rotation, and/or the holding vessel does not include any baffles.

22. The system of claim 20, wherein the dispersion element is conical.

* * * * *